United States Patent
Moldt et al.

[11] Patent Number: 6,100,275
[45] Date of Patent: Aug. 8, 2000

[54] 8-AZABICYCLO[3.2.1.]OCT-2-ENE DERIVATIVES, THEIR PREPARATION AND USE

[75] Inventors: Peter Moldt, Humlebaek; Jørgen Scheel-Kruger, Glostrup; Gunnar M. Olsen; Elsebet Østergaard Nielsen, both of Copenhagen, all of Denmark

[73] Assignee: Neurosearch A/S, Ballerup, Denmark

[21] Appl. No.: 09/043,294

[22] PCT Filed: Oct. 11, 1996

[86] PCT No.: PCT/EP96/04449

§ 371 Date: May 18, 1998

§ 102(e) Date: May 18, 1998

[87] PCT Pub. No.: WO97/13770

PCT Pub. Date: Apr. 17, 1997

[30] Foreign Application Priority Data

Oct. 13, 1995 [DK] Denmark .................................. 1156/95

[51] Int. Cl.⁷ .................... A01N 43/42; C07D 451/04; C07D 401/04
[52] U.S. Cl. .................... 514/304; 546/124; 546/125
[58] Field of Search ............... 514/304; 546/124, 546/125

[56] References Cited

U.S. PATENT DOCUMENTS

| | | | |
|---|---|---|---|
| 3,133,073 | 5/1964 | Archer et al. | 760/292 |
| 3,657,257 | 4/1972 | Helsley et al. | 260/292 |
| 4,132,710 | 1/1979 | Gauthier et al. | 546/63 |
| 4,180,669 | 12/1979 | Winn | 546/420 |
| 5,374,636 | 12/1994 | Moldt et al. | 514/304 |
| 5,418,224 | 5/1995 | Sauerberg et al. | 514/205 |
| 5,731,317 | 3/1998 | Lu et al. | 514/28 |

FOREIGN PATENT DOCUMENTS

| | | |
|---|---|---|
| 015002 | 3/1980 | European Pat. Off. |
| 0518805A1 | 12/1992 | European Pat. Off. |
| 49833 1A1 | 12/1992 | European Pat. Off. |
| 60435 4A2 | 6/1994 | European Pat. Off. |
| 2143587 | 3/1972 | Germany . |
| P211861 | 6/1995 | Hungary . |
| 2247886 | 3/1992 | United Kingdom . |
| 24788 6A | 3/1992 | United Kingdom . |
| WO9 203433 | 3/1992 | WIPO . |
| WO9 420496 | 9/1994 | WIPO . |
| WO9 426274 | 11/1994 | WIPO . |
| 9528401A1 | 10/1995 | WIPO . |

OTHER PUBLICATIONS

Perregaard, et al., J. Med. Chem., 38: 1998–2008 (1995).
Repke, et al., J. Org. Chem., 59: 2164–2171 (1994).
Freter, et al., J. Org. Chem., 40: 2525–2529 (1975).
Lyle, et al., J. Org. Chem., 35: 802–805 (1970).
Clarke, Robert et al., J. of Med. Chem., vol. 16, No. 11 (1973) pp.1260–1267.
Davies, Huw M.L. et al., J. of Med. Chem., vol. 37, (1994) pp. 1262–1268.
Davies, Huw M.L. et al., Euro. J. of Pharm. –Mole. Pharm. Sec., vol. 244, (1993) pp. 93–97.
Bennett, Barbara A. et al., J. of Pharm. And Exp. Thera., vol. 272, No. 3, (1995) pp. 1176–1186.
Fontenla, J. et al., Arch. De Farmacol. y. Toxicol., (1984) pp. 151–160.
Blommer, J. C. et al., Br. J. Clin. Pharmac., vol. 33, (1992) pp. 521–523.
Swain C. J. et al., J. Med. Chem., vol. 34, (1991) pp. 140–151.

*Primary Examiner*—Johann Richter
*Assistant Examiner*—Dominic Keating
*Attorney, Agent, or Firm*—Birch, Stewart, Kolasch & Birch, LLP

[57] ABSTRACT

A compound having the formula,

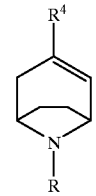

or any of its enantiomers or any mixture thereof, or a pharmaceutically acceptable salt thereof;
wherein
R is hydrogen, alkyl, alkenyl, alkynyl, cycloalkyl, cycloalkylalkyl or 2-hydroxyethyl; and
$R^4$ is
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;
benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl.

The compounds possess valuable pharmaceutical properties as monoamine neurotransmitter re-uptake inhibitors.

9 Claims, No Drawings

8-AZABICYCLO[3.2.1.]OCT-2-ENE DERIVATIVES, THEIR PREPARATION AND USE

This application is the national phase under 35 U.S.C. §371 of prior PCT International Application No., PCT/EP96/04449, which has an International filing date of Oct. 11, 1996, which designated the United States of America, the entire contents of which are hereby incorporated by reference.

The present invention relates to novel 8-azabicyclo [3.2.1]oct-2-ene derivatives which are monoamine neurotransmitter, i.e dopamine, serotonin and noradrenaline, re-uptake inhibitors. In particular, the present invention relates to novel 8-azabicyclo-[3.2.1]oct-2-ene derivatives which are potent serotonin re-uptake inhibitors and therefore useful in the treatment of disorders or diseases such as depression and related disorders, obsessive compulsive disorders, panic disorders, memory deficits, attention deficit hyperactivity disorder, obesity, anxiety and eating disorders.

BACKGROUND OF THE INVENTION

Monoamine neurotransmitters (i.e. serotonin, dopamine, and noradrenaline) are released into the synaptic cleft in order to stimulate postsynaptic receptor activity. The removal (or inactivation) of monoamine neurotransmitters occurs mainly by a reuptake mechanism into presynaptic terminals. By inhibiting the re-uptake an enhancement of the physiological activity of monoamine neurotransmitters occur.

Noradrenalin and serotonin re-uptake inhibitors are currently used as pharmaceuticals in anti-depressant therapy (Desipramine, Nortriptyline, and Protriptyline are inhihibitors of noradrenaline-reuptake and Imipramine and Amitriptyline are mixed serotonine-reuptake and noradrenaline-reuptake inhibitors).

The pathophysiology of major affective illness is poorly understood, and several neurotransmitters have been implicated in the pathophysiology of major depression. However, several lines of preclinical and clinical evidence indicate that an enhancement of serotonin-mediated neurotransmission might underlie the therapeutic effect of the most recent and currently used drugs in anti-depressant therapy, such as fluoxetine, citalopram and Paroxetine.

Paradoxical serotonin re-uptake inhibitors inhibit the serotonin transporter within minutes whereas their full antidepressant effect is seen only after three to four weeks of treatment, indicating that re-uptake inhibition per se is not responsible for the antidepressant response, but rather that further adaptive changes underlie and/or contribute to their therapeutic effect. The delayed onset of anti-depressant effect is considered to be a serious drawback to currently used monoamine re-uptake inhibitors.

The compounds provided herewith are potent serotonin (5-hydroxy-tryptamine, 5-HT) re-uptake inhibititors. The compounds of the invention also have noradrenaline and dopamine re-uptake inhibiting activity but the serotonin re-uptake inhibiting activity of the compounds of the invention is stronger than the dopamine re-uptake inhibiting activity of the compounds.

Further, a strong dopamine re-uptake inhibiting activity is currently considered with the risk of undesirable central stimulating effects. On the other hand, an activating effect on the mesolimbic dopamine system is currently believed to underlay the commen mechanism of current antidepressant treatment by a mechanism which enhances the endogenous reward system. Compounds with a strong serotonin re-uptake inhibiting activity combined with a well balanced dopamine re-uptake inhibiting activity may therefore provide agents with a rapid onset of anti-depressant effect.

The serotonergic neural system of the brain have been shown to influence a variety of physiologic functions, and the compounds of the present invention are believed to have the ability to treat in mammals, including humans, a variety of disorders associated with these neural systems such as eating disorders, depression, obcessive compulsive disorders, panic disorders, alcoholism, pain, memory deficits and anxiety. Therefore, the present invention also provides methods of treating several disorders linked to decreased neurotransmission of serotonin in mammals. Included among these disorders are depression and related disorders such as pseudodementia or Ganser's syndrome, migraine pain, bulimia, obesity, pre-menstrual syndrome or late luteal phase syndrome, alcoholism, tobacco abuse, panic disorder, anxiety, post-traumatic syndrome, memory loss, dementia of ageing, social phobia, attention deficit hyperactivity disorder, chronic fatigue syndrome, premature ejaculation, erectile difficulty, anorexia nervosa, disorders of sleep, autism, mutism or trichotillomania.

OBJECTS OF THE INVENTION

It is an object of the present invention to provide novel 8-azabicyclo[3.2.1]oct-2-ene derivatives which are monoamine neurotransmitter re-uptake inhibitors. In particular it is an object of the present invention to provide potent serotonin re-uptake inhibitors.

Another object of the invention is to provide novel pharmaceutical compositions containing the novel 8-azabicyclo[3.2.1]oct-2-ene derivatives which are useful for the treatment of disorders or diseases responsive to the monoamine neurotransmitter re-uptake inhibiting activity and in particular the strong serotonin re-uptake inhibiting activity of the compounds of the invention. Such diseases or disorders includes depression and related diseases.

Still another object of the invention is to provide a method of treating diseases or disorders responsive to the inhibition of monoamine neurotransmitter re-uptake and in particular serotonin re-uptake, such as depression and related diseases, by administering a therapeutically effective amount of one or more of the novel 8-azabicyclo[3.2.1]oct-2-ene derivatives to a living animal body, including a human.

Other objects will become apparent hereinafter to one skilled in the art.

THE PRESENT INVENTION

The invention then, inter alia, comprises the following, alone or in combination:

A compound having the formula,

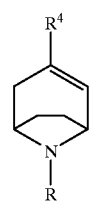

or any of its enantiomers or any mixture thereof, or a pharmaceutically acceptable salt thereof;
wherein R is hydrogen, alkyl, alkenyl, alkynyl, cycloalkyl, cycloalkylalkyl or 2-hydroxyethyl; and R⁴ is
phenyl which may be substituted one or more times with substituents selected from the group consisting of halogen, CF₃, CN, alkoxy, cycloalkoxy, alkyl, cycloalkyl, alkenyl, alkynyl, amino, nitro, heteroaryl and aryl;

3,4-methylenedioxyphenyl;

benzyl which may be substituted one or more times with substituents selected from the group consisting of halogen, CF₃, CN, alkoxy, cycloalkoxy, alkyl, cycloalkyl, alkenyl, alkynyl, amino, nitro, heteroaryl and aryl;

heteroaryl which may be substituted one or more times with substituents selected from the group consisting of halogen, CF₃, CN, alkoxy, cycloalkoxy, alkyl, cycloalkyl, alkenyl, alkynyl, amino, nitro, heteroaryl and aryl; or naphthyl which may be substituted one or more times with substituents selected from the group consisting of halogen, CF₃, CN, alkoxy, cycloalkoxy, alkyl, cycloalkyl, alkenyl, alkynyl, amino, nitro, heteroaryl and aryl;

a compound as above which is (±)-3-(3,4-Dichlorophenyl)-8-methyl-8-azabicyclo[3.2.1]oct-2-ene, (±)-3-(4-chlorophenyl)-8-methyl-8-azabicyclo[3.2.1]oct-2-ene, or (±)-3-(3,4-Dichlorophenyl)-8-azabicyclo[3.2.1]oct-2-ene, or a pharmaceutically acceptable addition salt thereof;

a pharmaceutical composition, comprising a therapeutically effective amount of a compound as above together with at least one pharmaceutically acceptable carrier or diluent;

the use of a compound as above for the manufacture of a medicament for the treatment of a disorder or disease of a living animal body, including a human, which disorder or disease is responsive to the inhibition of monoamine neurotransmitter re-uptake in the central nervous system;

the use of a compound as above for the manufacture of a medicament for the treatment of a disorder or disease of a living animal body, including a human, which disorder or disease is responsive to the inhibition of serotonin re-uptake in the central nervous system;

the use of a compound as above for the manufacture of a medicament for the treatment of depression and related disorders such as pseudodementia or Ganser's syndrome, obsessive compulsive disorders, panic disorders, memory deficits, attention deficit hyperactivity disorder, obesity, anxiety and eating disorders;

the use as above wherein the compound employed is (±)-3-(3,4-Dichlorophenyl)-8-methyl-8-azabicyclo[3.2.1]oct-2-ene, (±)-3-(4-chlorophenyl)-8-methyl-8-azabicyclo[3.2.1]oct-2-ene, or (±)-3-(3,4-Dichlorophenyl)-8-azabicyclo[3.2.1]oct-2-ene, or a pharmaceutically acceptable addition salt thereof;

a method of treating a disorder or disease of a living animal body, including a human, which disorder or disease is responsive to the inhibition of monoamine neurotransmitter re-uptake, comprising the step of administering to such a living animal body, including a human, in need thereof a therapeutically effective amount of a compound as above;

a method of treating a disorder or disease of a living animal body, including a human, which disorder or disease is responsive to the inhibition of serotonin re-uptake, comprising the step of administering to such a living animal body, including a human, in need thereof a therapeutically effective amount of a compound as above;

the method as above wherein depression and related disorders such as pseudodementia or Ganser's syndrome, obsessive compulsive disorders, panic disorders, memory deficits, attention deficit hyperactivity disorder, obesity, anxiety or eating disorders are treated; and a method for the preparation of a compound as above comprising the step of dehydrating a compound having the formula

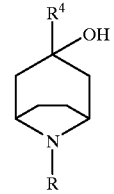

wherein R and R⁴ is as set forth above and thereafter optionally forming a pharmaceutically acceptable addition salt thereof.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, 1,2-, 2,3-, or 3,4-butenyl.

Alkynyl means a group of from two to six carbon atoms, including at least one triple bond, for example, but not limited to ethynyl, 2,3-propynyl, 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Cycloalkoxy is O-cycloalkyl, wherein cycloalkyl is as defined above.

Amino is NH₂ or NH-alkyl or N-(alkyl)₂, wherein alkyl is as defined above.

Heteroaryl is suitably a 5- or 6-membered heterocyclic monocyclic group. Such a heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol- 3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl.

Aryl is an aromatic hydrocarbon, such as phenyl or naphthyl.

I.p. means intraperetoneally, which is a well known route of administration.

P.o. means peroral, which is a well known route of administration.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that some compounds of the present invention contain chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

The following scheme illustrates one method by which the compounds of the invention can be prepared:

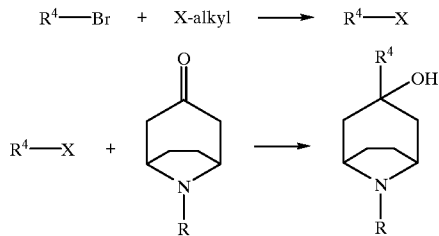

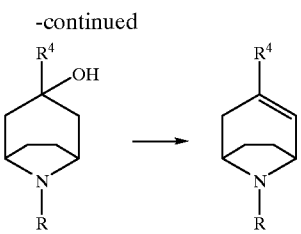

The substituents R and $R^4$ in the reaction-scheme is as defined above and X is Li, MgBr or any other type of functionality suitable for generating a carbanion as its counterpart.

The processes in the reaction scheme above is carried out in conventional manner. The dehydration of the alcohol is affected using acids such as hydrochloric or sulfuric acid or other conventional dehydrating agents such as for example $P_2O_5$, or $SOCl_2$.

A compound of the invention can be converted to another compound of the invention using conventional methods.

Starting materials for the processes described in the present patent application are known or can be prepared by known processes from commercially available materials.

The products of the reactions described herein are isolated by conventional means such as extraction, crystallization, distillation, chromatography, and the like.

Biology

The compounds of the invention have been tested for their ability to inhibit reuptake of dopamine(DA) noradrenaline (NA) and serotonin(5-HT) in synaptosomes.

Background:

Specific neurotransmitter transporters/uptake sites on nerve terminals presumably function to terminate neuronal signaling by removing the neurotransmitters dopamine, noradrenaline and serotonin, respectively, from the synaptic cleft. The activity of the transporter integral proteins can be measured in vitro by synaptosomal uptake of $^3$H-dopamine, $^3$H-noradrenaline and $^3$H-serotonine, respectively.

In vitro Inhibition of $^3$H-dopamine ($^3$H-DA) Uptake in Striatal Synaptosomes Tissue preparations: Preparations are performed at 0–4° C. unless otherwise indicated. Corpi striati from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-DA (1 nM, final concentration), mixed and incubated for 25 min at 37° C. Non-specific uptake is determined using benztropine (10 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-DA by 50%).

In vitro Inhibition of $^3$H-noradrenaline ($^3$H-NA) Uptake in Hippocampal Synaptosomes Tissue preparation: Preparations are performed at 0–4° C. unless otherwise indicated. Hippocampi from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (2000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 0.97 mM $CaCl_2$, 10 mM glucose and 1 mM ascorbic acid.

Assay: Aliquots of 4.0 ml tissue suspension are added to 100 μl of test solution and 100 μl of $^3$H-NA (1 nM, final concentration), mixed and incubated for 90 min at 37° C. Non-specific uptake is determined using desipramine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-NA by 50%).

In vitro Inhibition of $^3$H-5-hydroxytryptamine ($^3$H-5-HT, serotonin) Uptake in Cortical Synaptosomes Tissue preparation: Preparations are performed at 0–4° C. unless otherwise indicated. Cerebral cortices from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-5-HT by 50%).

Test results obtained by testing a selected compound of the present invention appear from the below table:

TABLE 2

| Test compound | DA-uptake $IC_{50}$(μM) | NA-uptake $IC_{50}$(μM) | 5-HT-uptake $IC_{50}$(μM) |
|---|---|---|---|
| (±)-3-(3,4-Dichlorophenyl)-8-methyl-8-azabicyclo[3.2.1]oct-2-ene | 0.079 | 0.026 | 0.0047 |

The results presented above show that the compounds are in vitro inhibitors of monoamine neurotransmitter re-uptake, in particular serotonin re-uptake.

The compounds of the invention have also been tested in the following test for antidepressant activity.

Tail Suspension

Background:

A decrease in the immobility time by mice suspended in their tail is seen after systemic administration of central stimulants and by antidepressants (Steru, L., Chermat, R., Thierry, B. & Simon, P. (1985) The tail suspension test: A new method for screening antidepressants in mice. Psychopharmacology 85:367–370.).

Method:

Female NMRI mice (20–25 g) habituated to the room (12 hours light/dark) for at least 16 hours and housed 25 per cage are used. The mice are suspended by the tail with adhesive tape to a rod 30 cm above the lab. bench 30 min after an oral administation of vehicle or drug. For the next 6 min the accumulated duration of immobility defined as no movements by the body or extremities (however head movements are not defined as movements) are noted. Six mice per dose are used.

Saline or vehicle treated mice have immobility time scores between 160–180 sec in average. An $ED_{50}$-value is calculated by graphical interpolation from at least 3 doses as the dose reducing the immobility to 100 sec.

$ED_{50}$ is 0.96 mg/kg for the compound (±)-3-(3,4-Dichlorophenyl)-8-methyl-8-azabicyclo[3.2.1]oct-2-ene.

The results presented above, predict a potent antidepressive activity of the compound of the invention.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantifies of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of the invention are extremely useful in the treatment of depression and related disorders due to their serotonin and dopamine uptake-inhibiting activity together with their low degree of undesired side-effects. These properties make the compounds of this invention extremely useful in the treatment of depression and related disorders, obsessive compulsive disorders, panic disorders, memory deficits, attention deficit hyperactivity disorders, obesity, anxiety and eating disorders as well as other disorders sensitive to the serotonin and dopamine uptake-inhibiting activity of the compounds of the present invention. The compounds of this invention may accordingly be administered to a living animal body, including a human, in need of treatment, alleviation, or elimination of an indication associated with or responsive to dopamine and serotonine uptake-inhibiting activity. This includes especially parkinsonism, depression, obesity, narcolepsy, and drug abuse.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

3-(3,4-Dichlorophenyl)-8-methyl-8-azabicyclo [3.2.1]octan-3-ol

A stirred solution of 1-bromo-3,4-dichlorobenzene (178.6 g, 0.8 mol) in anhydrous diethyl ether (1430 mL) under an argon atmosphere was cooled to −70° C. A solution of n-butyllithium in hexanes (310 mL 2.5 M; 0.78 mol) was added slowly while the temperature was kept below −65° C. (addition time=1 hour). The resulting solution was stirred for another 30 minutes at −70° C. followed by addition of a solution of 8-methyl-8-azabicyclo[3.2.1]octan-3-one (50 g, 0.36 mol) in anhydrous tetrahydrofuran (360 mL). The temperature was kept below −50° C. during the addition which took approximately one hour. The resulting solution was stirred at −50° C. for two hours followed by a addition of water (215 mL) over 15 minutes and 4M HCl (360 mL) over 25 minutes. The temperature reached −20° C. by the end of the addition. The organic phase was discharged and the aqueous phase was washed once with diethyl ether (500 mL). Concentrated $NH_4OH$ (approximately 200 mL) was added to the aqueous phase to pH=10 which resulted in precipitation of the title compound. A crude product was isolated by filtration which was suspended twice in water (2×300 mL) and finally dried under a lamp yielding the title compound as a white solid (88 g, 86%), m.p. 179.3–180.5° C.

The following compounds was prepared analogously:

3-(4-Chlorophenyl)8-methyl-8-azabicyclo[3.2.1] octan-3-ol

The title compound was prepared from 4-bromochlorobenzene (15.4 g, 81 mmol), n-butyllithium in hexanes (31 mL 2.5 M; 78 mmol) and 8-methyl-8-azabicyclo[3.2.1]-octan-3-one (5 g, 36 mmol). Yield 5.7 g (63%) as a white solid, m.p. 186.3–187° C.

8-Methyl-3-phenyl-8-azabicyclo[3.2.1]octan-3-ol

The title compound was prepared from bromobenzene (42.1 mL, 0.4 mol), n-butyllithium in hexanes (156 mL, 2.5 M, 0.39 mol) and 8-methyl-8-azabicyclo[3.2.1]-octan-3-one (25 g, 0.18 mol). Yield 14 g (36%), m.p. 157–159° C.

8-Methyl-3-(4-methylphenyl)-8-azabicyclo[3.2.1] octan-3-ol

The title compound was prepared from 4-bromotoluene (13.9 g, 81.4 mmol), n-butyllithium in hexanes (31.2 mL, 2.5 M; 78 mmol) and 8-methyl-8-azabicyclo[3.2.1]-octan-3-one (5 g, 35.9 mmol) in anhydrous tetrahydrofuran (40 mL). Yield 3.5 g (42%) as a white solid, m.p. 247–249° C.

3-(4-Methoxyphenyl)-8-methyl-8-azabicyclo[3.2.1] octan-3-ol

The title compound was prepared from 4-bromoanisole (15.1 g, 80.5 mmol), n-butyllithium in hexanes (31.2 mL, 2.5 M; 77.9 mmol) and 8-methyl-8-azabicyclo-[3.2.1]octan-3-one (5 g, 36 mmol) in anhydrous tetrahydrofuran (40 mL). Yield 2.1 g (24%), m.p. 161.8–162.3° C.

8-Methyl-3-(4-trifluoromethylphenyl)-8-azabicyclo [3.2.1]octan-3-ol

The title compound was prepared from 4-bromobenzotrifluoride, n-butyllithium in hexanes (31.2 mL, 2.5M; 77.9 mmol) and 8-methyl-8-azabicyclo[3.2.1] octan-3-one (5 g, 36 mmol). Yield 6.2 g (60%) as a yellow solid, m.p. 189.2–190.5° C.

3-(4-Fluorophenyl)-8-methyl-8-azabicyclo[3.2.1] octan-3-ol

The title compound was prepared from 4-bromofluorobenzene (26.3 g, 0.15 mol), n-butyllithium in hexanes (60 mL, 2.5 M; 0.15 mol) and 8-methyl-8-azabicyclo-[3.2.1]octan-3-one (10 g, 71.7 mmol). Yield 9.9 g (59%), m.p. 168.5–170° C.

EXAMPLE 2

(±)-3-(3,4-Dichlorophenyl)-8-methyl-8-azabicyclo [3.2.1]oct-2-ene

To a stirred solution of 3-(3,4-dichlorophenyl)-8-methyl-8-azabicyclo[3.2.1]octan-3-ol (50 g, 0.17 mol) in glacial acetic acid (160 mL) at room temperature was added concentrated hydrochloric acid (50 mL). The reaction mixture was heated at reflux. The starting material was consumed after 20 minutes and the reaction mixture was poured into approximately 1.5 L of crushed ice. The resulting aqueous solution was added concentrated NH$_4$OH (approximately 325 mL) to pH=9–10 resulting in precipitation of a sticky solid. The mixture was decanted and the reminiscence was triturated in water (1.5 L) resulting in a crystalline crude product. The crude product was washed a last time with water (300 mL) and was dried in a fume hood yielding the title compound as an off-white solid, m.p. 44–52° C.

The following compounds was prepared analogously:

(±)3-(4-Chlorophenyl)-8-methyl-8-azabicyclo[3.2.1] oct-2-ene Malonate

The title compound was prepared from 3-(4-chlorophenyl)-8-methyl-8-azabicyclo[3.2.1]octan-3-ol (4 g, 16 mmol), glacial acetic acid (15 mL) and concentrated hydrochloric acid (15 mL). Yield of free base (3.6 g, 97%). Some of the free base (1.44 g, 6 mmol) was dissolved in ethanol (96%) and added malonic acid (0.62 g, 6 mmol) in ethanol (96%). The resulting solution was concentrated to an oil, the oil was triturated in diethyl ether, the title compound precipitated as powder and was isolated by filtration. Yield (1.4 g, 71%) as white crystals m.p. 100.8–102.1° C.

(±)-8-Methyl-3-phenyl-8-azabicyclo[3.2.1]oct-2-ene Malonate

The title compound was prepared from 8-methyl-3-phenyl-8-azabicyclo[3.2.1]octan-3-ol (8 g, 37 mmol), glacial acetic acid (25 mL) and concentrated hydrochloric acid (8 mL). The free base of the title compound (7.4 g, 37 mmol) was dissolved in absolute ethanol (20 mL) and added malonic acid (3.9 g, 37.5 mmol), the solution was heated at reflux for a couple of minutes, some impurities was removed by filtration while the solution was still hot, the solution was cooled and kept at 5° C. for at while, then seeded with a crystal and precipitation of the title compound began, after 2 hours at 5° C., the title compound was isolated by filtration, the crystals was washed with cold absolute ethanol (10 mL). Yield 5.9 g (53%), m.p. 131–131.8° C.

(±)-8-Methyl-3-(4-methylphenyl)-8-azabicyclo [3.2.1]oct-2-ene Fumarate

The title compound was prepared from 8-methyl-3-(4-methylphenyl)-8-azabicyclo[3.2.1]octan-3-ol (3.4 g, 14.7 mmol), glacial acetic acid (11 mL) and concentrated hydrochloric acid (11 mL). The free base of the title compound was dissolved in diethyl ether and added fumaric acid (1.3 g, 11.2 mmol) in methanol. The resulting solution was concentrated to dryness, the residue was trituated in diethyl ether, the title compound precipitated as powder and was isolated by filtration. Yield 2.46 g (51%) m.p. 156.8–157.4° C.

(±)-3-(4-Methoxyphenyl)-8-methyl-8-azabicyclo [3.2.1]oct-2-ene Fumarate

The title compound was prepared from 3-(4-methoxyphenyl)-8-methyl-8-azabicyclo[3.2.1]octan-3-ol (2 g, 8 mmol), glacial acetic acid (6.4 mL) and concentrated hydrochloric acid (6.4 mL). The free base of the title compound was dissolved in ethanol (96%) and added fumaric acid (0.8 g, 6.9 mmol), no precipitate appeared, the solution was concentrated to dryness, the residue was crystallised from absolute ethanol. Yield 1.1 g (40%) as white crystals m.p. 167.3–168.7° C.

(±)-8-Methyl-3-(4-trifluoromethylphenyl)-8-azabicyclo[3.2.1]oct-2-ene Malonate

The title compound was prepared from 8-methyl-3-(4-trifluoromethylphenyl)-8-azabicyclo[3.2.1]octan-3-ol (5 g, 17.5 mmol), glacial acetic acid (16 mL) and concentrated hydrochloric acid (16 mL). The free base of the title compound was dissolved in ethanol (96%) and added malonic acid (1.17 g, 11.2 mmol) in ethanol (96%), the solution was concentrated to dryness, and the residue was trituated in diethyl ether, the title compound precipitated as powder and was isolated by filtration. Yield 3.9 g (60%), m.p. 106.7–107.8° C.

(±)-3-(4-Fluorophenyl)-8-methyl-8-azabicyclo[3.2.1] oct-2-ene Malonate

The title compound was prepared from 3-(4-fluorophenyl)-8-methyl-8-azabicyclo[3.2.1]octan-3-ol (4.7 g, 20 mmol), glacial acetic acid (20 mL) and concentrated hydrochloric acid (20 mL). The free base of the title compound was dissolved in isopropanol and malonic acid (1.7 g, 16.3 mmol) was added, after a while the title compound precipitated as powder and was isolated by filtration. Yield 4.6 g (72%), m.p. 122.2–123° C.

EXAMPLE 3

(±)-3-(4-Chlorophenyl)-8-azabicyclo[3.2.1]oct-2-ene Malonate

To a stirred solution of 3-(4-chlorophenyl)-8-methyl-8-azabicyclo[3.2.1]oct-2-ene (2 g, 8.5 mmol) in anhydrous 1,2-dichloroethane (20 mL) under a nitrogen atmosphere was added 1-chloroethyl chloroformate (1.25 mL, 11.6 mmol). The reaction mixture was heated at reflux overnight, then added 1-chloroethyl chloroformate (1 mL, 9.3 mmol), once again the reaction mixture was heated at reflux overnight. The reaction mixture was concentrated to an oil, the oil was dissolved in methanol (25 mL), this solution was heated at reflux for 2 hours and then concentrated to an oil. The residue was dissolved in water and added concentrated NH$_4$OH until pH=10, the water phase was extracted with diethyl ether. The organic phase was dried with magnesium sulphate and concentrated to dryness. The residue was chromatographed over silica gel (dichloromethane/acetone/methanol, 4/1/1 (v/v)). The product fractions was concentrated to an oil, the oil was dissolved in ethanol (96%) and malonic acid (0.55 g, 5.3 mmol) in ethanol (96%) was added, this solution was concentrated to an oil, the oil was trituated in diethyl ether, the title compound precipitated as powder and was isolated by filtration. Yield (1.32 g, 48%), m.p. 136.1–138° C.

The following compound was prepared analogously:

(±)-3-(4-Fluorophenyl)-8-azabicyclo[3.2.1]oct-2-ene Malonate

The title compound was prepared from (±)-3-(4-fluorophenyl)-8-methyl-8-azabicyclo[3.2.1]oct-2-ene (1.6 g, 7.37 mmol) and 1-chloroethyl chloroformate (1.2 mL, 1.6g, 11 mmol). The free base of the title compound was dissolved in isopropanol and added malonic acid (0.43 g, 4.1 mmol), the title compound precipitated from this solution and was isolated by filtration. Yield 1.14 g (50%) m.p. 132.2–132.6° C.

EXAMPLE 4

(±)-3-(3,4-Dichlorophenyl)-8-azabicyclo[3.2.1]oct-2-ene Malonate

To a stirred solution of (±)-3-(3,4-dichlorophenyl)-8-methyl-8-azabicyclo[3.2.1]oct-2-ene (10 g, 37 mmol) in anhydrous 1,2-dichloroethane (100 mL) under a nitrogen atmosphere was added 1-chloroethyl chloroformate (8 mL, 10.6 g, 74 mmol), the reaction mixture was heated at reflux overnight then added 1-chloroethyl chloroformate (4 mL, 5.3 g, 37 mmol) and heated at reflux for 4 hours. The reaction mixture was concentrated to dryness. The residue was dissolved in methanol, and the reaction mixture was heated at reflux for 2 hours and then concentrated to dryness. The residue was chromatographed over silica gel (eluted with dichloromethane/methanol (9/1, v/v) then dichloromethane/acetone/methanol (4/1/1, v/v) and at last with methanol). The product fractions was concentrated to dryness, the residue (1.8 g the rest was start compound) was dissolved in glacial acetic acid (10 mL) and added water (5 mL) and zinc powder (1 g, 15.2 mmol), the reaction mixture was stirred overnight at room temperature. The reaction mixture was poured into water, and concentrated $NH_4OH$ was added until pH=10, the water phase was extracted with diethyl ether, the organic phase was washed with water, dried with magnesium sulphate and evaporated to an oil. The oil crystallised upon standing at room temperature. The solid was dissolved in ethanol (96%) and 4M sodium hydroxide (5 mL) was added and the reaction mixture was heated at reflux overnight. Then more 4M sodium hydroxide (10 mL) was added and once again was the reaction mixture was heated at reflux overnight. Then more 4M sodium hydroxide (10 mL) was added and the reaction mixture was heated at reflux for 4 hours. The reaction mixture was concentrated until no more ethanol was left, water was added during concentration to maintain the volume of the solution approximately constant. The resulting solution was extracted with diethyl ether. The organic phase was dried with magnesium sulphate and evaporated to a brown oil. The oil was flash chromatographed over silica gel (50 g) (dichloromethane/acetone/methanol 4/1/1 (v/v)). The product fractions was concentrated to an oil. The oil was dissolved in ethanol (96%) and added malonic acid (0.3 g, 0.29 mmol). The title compound precipitated from this solution and was isolated by filtration. Yield 0.65 g (5.5%) mp. 110–112° C.

We claim:
1. A compound having the formula,

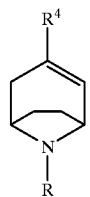

or any of its enantiomers or any mixture thereof, or a pharmaceutically acceptable salt thereof;
 wherein
  R is hydrogen, alkyl, alkenyl, alkynyl, cycloalkyl, cycloalkylalkyl or 2-hydroxyethyl; and
  $R^4$ is
   phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
   3,4-methylenedioxyphenyl;
   benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
   heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
   naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl with the proviso that when R is hydrogen, $R^4$ is not phenyl or 4-fluorophenyl;
   if R is methyl, then $R^4$ is not phenyl, methylphenyl 4-methoxyophenyl, or phenyl which is mono-substituted with halogen, ethyl or $CF_3$;
   if R is ethyl, then $R^4$ is not phenyl; and
   if R is octyl, then $R^4$ is not phenyl.
2. A compound which is
(±)-3-(3,4-Dichlorophenyl)-8-methyl-8-azabicyclo[3.2.1]oct-2-ene,
(±)-3-(3,4-Dichlorophenyl)-8-azabicyclo[3.2.1]oct-2-ene,
(±)-8-methyl-3-(4-methoxyphenyl)-8-azabicyclo[3.2.1]oct-2-ene,
(±)-8-methyl-3-(4-trifluoromethylphenyl)-8-azabicyclo[3.2.1]oct-2-ene,
(±)-3-(4-chlorophenyl)-8-azabicyclo[3.2.1]oct-2-ene, or
a pharmaceutically acceptable addition salt thereof.
3. A pharmaceutical composition, comprising a therapeutically effective amount of a compound of claim 1, together with at least one pharmaceutically acceptable carrier or diluent.
4. A method of inhibiting monoamine neurotransmitter reuptake in a living animal body, comprising the step of administering to said living animal body, in need thereof a therapeutically effective amount of a compound according to claim 1.
5. A method of inhibiting serotonin reuptake in a living animal body, comprising the step of administering to such a living animal body, in need thereof a therapeutically effective amount of a compound according to claim 1.
6. The method of claim 4 or 5 which is used to treat a disorder selected from the group consisting of depression, pseudodementia, Ganser's syndrome, obsessive compulsive disorders, panic disorders, memory deficits, attention deficit hyperactivity disorder, obesity, anxiety and eating disorders.
7. A method for the preparation of the compounds of claim 1 comprising the step of dehydrating a compound having the formula

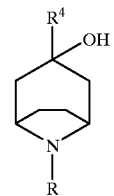

wherein R and $R^4$ is as defined in claim 1 and thereafter optionally forming a pharmaceutically acceptable addition salt thereof.
8. The method of claim 4 wherein said living animal body is a human.
9. The method of claim 5 wherein said living animal body is a human.

* * * * *